(12) United States Patent
Singh et al.

(10) Patent No.: US 7,858,126 B2
(45) Date of Patent: Dec. 28, 2010

(54) DERIVATIVES OF SANDALWOOD OIL AND SANTALOLS FOR TREATING COLD SORES AND HERPES

(75) Inventors: Chandra Ulagaraj Singh, San Antonio, TX (US); Jagaveerabhadra Rao Nulu, Austin, TX (US)

(73) Assignee: Trinity Laboratories Inc., San Antonio, TX (US)

( * ) Notice: Subject to any disclaimer, the term of this patent is extended or adjusted under 35 U.S.C. 154(b) by 0 days.

(21) Appl. No.: 11/896,327

(22) Filed: Aug. 31, 2007

(65) Prior Publication Data

US 2008/0058413 A1    Mar. 6, 2008

Related U.S. Application Data

(60) Provisional application No. 60/841,228, filed on Aug. 31, 2006.

(51) Int. Cl.
A01N 65/001    (2006.01)
(52) U.S. Cl. .................................................... 424/725
(58) Field of Classification Search ................. None
See application file for complete search history.

(56) References Cited

U.S. PATENT DOCUMENTS

| | | | |
|---|---|---|---|
| 3,970,706 A | 7/1976 | Julia | |
| 5,225,608 A | 7/1993 | Eilerman | |
| 5,248,503 A * | 9/1993 | Emanuel-King | 424/737 |
| 5,641,483 A * | 6/1997 | Beaulieu | 424/78.06 |
| 5,945,116 A | 8/1999 | Haque | |
| 6,132,756 A * | 10/2000 | Haque et al. | 424/430 |
| 6,280,751 B1 | 8/2001 | Fletcher | |
| 6,406,706 B1 | 6/2002 | Haque | |
| 6,573,251 B2 * | 6/2003 | Gautron et al. | 514/59 |
| 6,911,211 B2 | 6/2005 | Eini | |
| 7,087,228 B2 | 8/2006 | Goodman | |
| 7,238,514 B2 | 7/2007 | Matsuda | |
| 7,361,361 B2 * | 4/2008 | Luu et al. | 424/400 |
| 2002/0044977 A1 * | 4/2002 | Close | 424/725 |
| 2002/0098159 A1 | 7/2002 | Wei | |
| 2003/0040009 A1 | 2/2003 | Denny | |
| 2004/0071757 A1 | 4/2004 | Rolf | |
| 2004/0102429 A1 * | 5/2004 | Modak et al. | 514/184 |
| 2004/0109899 A1 | 6/2004 | Albahri | |
| 2005/0014730 A1 | 1/2005 | Carlson | |
| 2005/0019431 A1 | 1/2005 | Modak | |
| 2005/0214391 A1 | 9/2005 | Schultz | |
| 2006/0058238 A1 | 3/2006 | Laurent-Applegate | |
| 2006/0205679 A1 | 9/2006 | Streeper | |
| 2006/0275218 A1 | 12/2006 | Tamarkin | |
| 2007/0020342 A1 | 1/2007 | Modak | |
| 2007/0026056 A1 | 2/2007 | Rolf | |
| 2007/0087041 A1 | 4/2007 | Luu et al. | |

FOREIGN PATENT DOCUMENTS

| | | |
|---|---|---|
| EP | 000001632239 | 3/2006 |
| EP | 000001660056 | 5/2006 |
| WO | WO 0128339 | 4/2001 |
| WO | WO 03077811 | 9/2003 |
| WO | WO 2007075597 | 7/2007 |

OTHER PUBLICATIONS

Herbdata, 11 pages, 2009, "Oil of sandalwood".*
Shankaranarayana et al., Indian Perfumer, 31 (3), 1987, pp. 211-214.*
Shankaranarayana et al., Indian Perfumer, 28 (3 and 4), 1984, pp. 138-141.*

* cited by examiner

Primary Examiner—Michael V Meller
(74) Attorney, Agent, or Firm—Reed Smith LLP; John M. Hammond

(57) ABSTRACT

The present invention relates to the formulations of ester derivatives of sandalwood oil and santalol. These derivatives are capable of reverting to the active parent compound following enzymatic or chemical hydrolysis. These derivatives have a higher lipophilicity, lipid solubility and less irritation to the skin than the parent compound, and hence are better able to be incorporated into certain pharmaceutical formulations, including cream and ointment pharmaceutical formulations. The compounds of the present invention are set forth by the following formula:

The present invention generally pertains to a compound of formula (I):

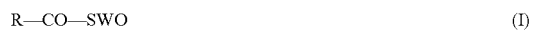

R—CO—SWO    (I)

wherein SWO refers to collectively the alcohols, including santalol, present in the sandalwood oil; wherein R is selected from alkyl groups of up to about 22 carbon atoms and aryl groups of up to about 22 carbon atoms and alkylene group of up to about 22 carbon atoms and an arylene group of up to about 22 carbon atoms. The alkyl, aryl and alkylene groups may be substituted or unsubstituted, branched or straight chains. In addition, R may contain heteroatoms and may be straight chained or branched.

Compounds of formula I are useful as anti-bacterial and anti-viral in mammals in vivo and have been contemplated to be used in the treatment of skin disease.

26 Claims, 1 Drawing Sheet

FIGURE 1. The Chemical Structures of Santalols.
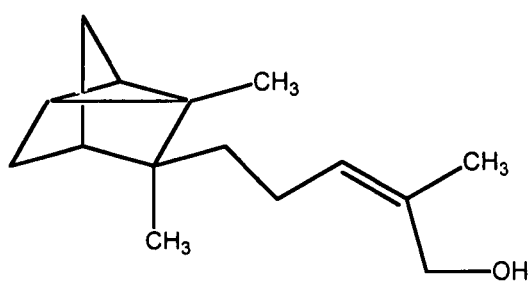
Alpha-Santalol
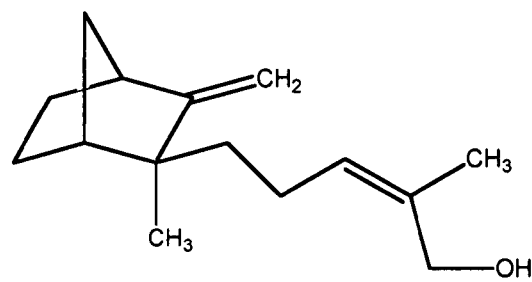
Beta-Santalol

DERIVATIVES OF SANDALWOOD OIL AND SANTALOLS FOR TREATING COLD SORES AND HERPES

CROSS-REFERENCE TO RELATED APPLICATIONS

This application claims the benefit of Provisional Patent Application Ser. No. 60/841,228, filed Aug. 31, 2006 by the present inventors.

FEDERALLY SPONSORED RESEARCH

None

SEQUENCE LISTING OR PROGRAM

None

FIELD OF INVENTION

This invention relates to the treatment of herpes. More specifically it relates to the treatment of herpes with sandalwood. Even more specifically it relates to the treatment of herpes with derivatives of sandalwood

BACKGROUND OF THE INVENTION

Oral herpes, an infection caused by the herpes simplex virus, is estimated to be present in 50 to 80 percent of the American adult population. Nearly 20 percent, over 50 million people, are infected with genital herpes, also caused by the herpes simplex virus, and the majority of these cases may be unaware they even have it. Studies show that more than 500,000 Americans are diagnosed with genital herpes each year, and the largest increase is occurring in young teens.

Cold sores, sometimes called fever blisters, are clusters of small blisters on the lip and outer edge of the mouth. The skin around the blisters is often red and inflamed. The blisters can break open, weep a clear fluid, and then scab over after a few days. Complete healing may take 7 to 10 days. Cold sores are caused by the herpes simplex virus (HSV). There are two types of herpes simplex virus (HSV). HSV-1 usually leads to lip and mouth sores (herpes labialis), while HSV-2 most often leads to genital herpes. However, both virus types can cause cold sores or genital herpes if skin comes into contact with either type. Cold sores are caused by the herpes simplex virus (HSV). There are two types of herpes simplex virus (HSV). HSV-1 usually leads to lip and mouth sores (herpes labialis), while HSV-2 most often leads to genital herpes. However, both virus types can cause cold sores or genital herpes if skin comes into contact with either type. Cold sores are estimated to be present in 50 to 80 percent of the American adult population. Nearly 20 percent, over 50 million people, are infected with genital herpes, also caused by the herpes simplex virus, and the majority of these cases may be unaware they even have it. Studies show that more than 500,000 Americans are diagnosed with genital herpes each year, and the largest increase is occurring in young teens.

There is no cure for cold sores and genital herpes to date. Efforts to develop a herpes vaccine by biotechnology companies are ongoing. Until an effective herpes vaccine or cure for HSV infection is found, the prevailing approach to treatment continues to be suppressive antiviral therapy.

Topical creams are commonly used to treat cold sores. Many are prescription medications that can slightly shorten the duration of cold sores, usually by just 1 to 2 days. Studies are ongoing to determine the effectiveness of these creams (Boon 2000). Some experts find that even when nonprescription topical creams are used frequently, every 2 hours during wake time, at the first sign of an outbreak, they may only speed recovery time by a few hours or a day (Habif 2004).

Penciclovir cream (such as Denavir) is an antiviral cream that may reduce healing time by 1 to 2 days, especially if the cold sore was triggered by sunlight exposure (Sacks 2001; Herpes 2003). It also reduces pain, itching, burning, and tenderness associated with cold sores. Penciclovir cream may cause side effects such as mild pain or stinging when it is applied. It is possible, although rare, that the cream may also cause a skin rash or headache.

Acyclovir ointment and cream are used up to six times a day for 10 days. Treatment with acyclovir ointment works best if it is used at the first sign of cold sore symptoms. The cream can improve healing time by up to ½ a day. Side effects of acyclovir ointment may include mild pain or stinging at the site of application. The cream may cause temporary skin irritation.

Tetracaine cream is a nonprescription topical anesthetic that lessens the physical sensation and can relieve pain and itching associated with cold sores. Initial studies show that tetracaine cream can reduce the healing time of cold sores by up to 2 days (Habif 2001). Tetracaine cream is applied to cold sores up to six times daily for best results. Pain and itching are relieved usually within 2 to 3 days after first applying tetracaine cream.

Docosanol 10% (Abreva) is a newer nonprescription cream that is safe and effective for treating cold sores. It is most effective when applied at the first signs of a cold sore outbreak (Sacks 2001). It is the first nonprescription cold sore medication approved by the U.S. Food and Drug Administration (FDA) to shorten healing time and duration of symptoms.

Valacyclovir was recently approved by the U.S. Food and Drug Administration (FDA) as a one-day treatment to reduce cold sore duration in people 12 years and older (Habif 2004). It is absorbed by the body much better than some other antiviral medications (such as acyclovir). Possible side effects include skin rash, allergic reaction, headache, dizziness, insomnia, depression, and fatigue.

Native to India, the sandalwood tree is used for many purposes; the wood for decorative carvings, the oil for fragrance in incense, perfumes, and soaps. Both its wood and oil have also been employed medicinally for a wide variety of conditions. In traditional Indian (Ayurvedic) medicine, sandalwood was used to treat gonorrhea and to decrease sex drive. Traditional Chinese medicine also lists sandalwood as a treatment for gonorrhea, as well as for stomachache and vomiting. In Europe, sandalwood was used to treat fever and pain. However, no clinical evidence exists to support any of these applications.

The main constituent of sandalwood oil is santalol. This primary sesquiterpene alcohol forms more than 90 percent of the oil and is present as a mixture of two isomers, α-santalol and β-santalol, the former predominating. The characteristic odor and medicinal properties of sandalwood oil are mainly due to the santalols. The other constituents reported in sandalwood oil include: the hydrocarbons santene, nor-tricycloekasantalene and α- and β-santalenes; the alcohols santenol and teresantalol; the aldehydes nor-tricycloekasantalal, and isovaleraldehyde; the ketones 1-santenone and santalone; and the acids teresantalic acid occurring partly free and partly in esterfied form, and α- and β-santalic acids. Table I sets forth the certain constituents of a fresh sandalwood oil.

TABLE I

Comparative composition of Sample of Sandalwood Oil

| Compound | Weight Percentage Composition |
| --- | --- |
| α-santalene | 0.82 |
| epi-β-santalene | 0.97 |
| β-santalene | 1.40 |
| α-santalal | 2.90 |
| cis-α-santalyl acetate | — |
| β-santalal | 0.56 |
| cis-β-santalyl acetate | — |
| cis-α-santalol | 50.0 |
| (Z)-trans-α-begamotol | 3.90 |
| epi-β-santalol | 4.10 |
| cis-β-santalol | 20.9 |
| trans-β-santalol | 1.50 |
| cis-lanceol | 1.70 |
| cis-nuciferol | 1.10 |
| spirosantalol | 1.20 |

The total alcohol content varies from 80% to 93% by weight. The santalol content also varies from species to species of *Santalum*. Table II sets forth the santalol content of various *Santalum* species.

TABLE II

Santalol content of various *Santalum* species

| | | Percentage composition | |
| --- | --- | --- | --- |
| *Santalum* Species | Origin | α-santalol | β-santalol |
| S. album (1)* | China | 50.0 | 18.1 |
| S. album (4) | India | 46.6-59.9 | 24.6-29.0 |
| S. album (5) | Indonesia | 7.1-48.6 | 8.7-25.2 |
| S. yasi (1) | Fiji | 54.0 | 32.8 |
| S. papuanum (1) | Papua, New Guinea | 26.3 | 15.5 |
| S. spicatum (3) | Australia | 27.9-35.3 | 4.0-29.2 |

*No. of samples

Germany's Commission E has approved sandalwood oil for the treatment of bladder infections, not to be used alone, but along with other therapies (Blumenthal 1998). Sandalwood oil is said to act as an antiseptic in the urinary system; if this is correct, it might help to rid the body of the bacteria that cause these infections (Leung 1996), but there is no reliable evidence as yet to verify this belief.

In test tube studies, sandalwood oil was found to slow the growth of herpes virus (Benencia 1999). An animal study found that components isolated from sandalwood caused responses similar to those seen with medications used to treat schizophrenia (Okugawa 1995). However, this evidence is far too weak to indicate that sandalwood is a useful treatment for either of these conditions. Sandalwood oil is also advertised for other therapeutic uses, including bronchitis, sore throat, and persistent cough. External application of a sandalwood paste is sometimes suggested for acne, skin rashes, or dry skin. None of these proposed uses, however, have been scientifically studied.

The safety of sandalwood oil has not been formally evaluated. Reported side effects include nausea and itching (Blumenthal 1998). Sandalwood paste applied externally has been reported to cause skin irritation on rare occasions. There is also one case report of a man developing a skin rash after burning large quantities of sandalwood incense (Sandra 1996; Sharma 1987; Hayakawa 1987).

The sandalwood oil displayed chemoprotective effects on 7,12-dimethylbenz(a)anthracene-(DMBA)-initiated and 12-O-tetradecanoyl phorbol-13-acetate(TPA)-promoted skin papillomas, and TPA-induced ornithine decarboxylase (ODC) activity in mice. Treatment with sandalwood oil or santalol significantly decreased papilloma incidence by 67%, multiplicity by 96%, and TPA-induced ODC activity by 70% (Dwivedi and Abu-Ghazaleh 1997; Dwivedi 2003). Kaur et al (2005) identify the apoptotic effect of -santalol, and define the mechanism of apoptotic cascade activated by this agent in A431 cells, which might be contributing to its overall cancer preventive efficacy in mouse skin cancer models. The sandalwood oil was found to enhance glutathione S-transferase (GST) activity and acid soluble sulphydryl (SH) levels in the liver of adult male Swiss albino mice, suggesting a possible chemopreventive action. (Banerjee et al. 1993).

U.S. Pat. No. 6,132,756 discloses the use of sandalwood oil for the treatment of warts caused by the human papillomavirus (HPV) in humans. U.S. Pat. No. 6,406,706 discloses the use of α- and β-santalols, or mixtures or derivatives thereof, to prepare medicaments for the treatment of viral-induced tumors i.e., warts caused by the human papillomavirus (HPV) in humans. U.S. Pat. No. 5,225,608 discloses substituted cyclohexanol compounds that are similar to beta-santalol and that possessing a sandalwood aroma, but lacks the carbon chains claimed by the present invention. U.S. Pat. No. 3,970,706 discloses a method of making alpha-santalol, but not a method of making an ester of santalol or using a santalol compound.

The chemical formula for α- and β-santalol is $C_{15}H_{24}O$ and the chemical structures are shown in FIG. 1. The chemical names for santalol (α- and β) are 2-methyl-5-(2,3-dimethyl-tricyclo[2.2.1.0(2.6)]hept-3-yl)pent-2-enol and 2-methyl-5-(2-methyl-3-methylenebicyclo[2.2.1]hept-2-yl)pent-2-enol, respectively.

Santalols may be obtained by fractional distillation of sandalwood oil, with the α- and β-isomers appearing in different ratios and with the α-isomer being more abundant. Santalol can be isolated from sandalwood oil by distillation under vacuum, BP 95° C./0.5 mm Hg. The santalols are colorless to pale yellow in appearance.

Santalols are commonly used in the flavor and fragrance industries and are considered woody, cedar-like, warm and herbaceous. They may be used in perfumes, baked goods, frozen dairy, soft candy, gelatin pudding, chewing gum and non-alcoholic beverages. As such, they are non-toxic and harmless when used either for external application on the skin or internal consumption for flavor.

Since sandalwood oil contains 80-90% of alcohol, excess application to the skin can cause irritation and itching. To eliminate the irritation and itching, the alcohols can be esterified as they are milder to the skin.

The purpose of the present application is to disclose the unexpected discovery that the esterified sandalwood oil and esterified santalols are extremely effective in treating cold sores and genital herpes in humans.

SUMMARY OF THE INVENTION

The present invention provides for certain novel ester derivatives of sandalwood oil and santalol that are highly lipophilic. The novel compounds set forth herein are enzymatically cleaved to the parent compound. Thus, the compounds set forth herein provide for a novel form of therapy of diseases amendable to treatment with sandalwood oil and santalol.

The novel ester derivatives of sandalwood oil and santalol of the present invention would have significant utility over sandalwood oil and existing derivatives currently described in the patent and scientific literature. In particular, in view of their high lipophilicity, non-irritation to the skin and stability, these new derivatives would be more bioavailable when administered topically compared to sandalwood oil or santalol. In addition, because of their stability and non-toxic nature, these agents can be made more readily available to the general pubic. The inventor has surprisingly and unexpectedly discovered that these ester derivatives have therapeutic utility in treating cold sores and genital herpes in humans.

The present invention generally pertains to a compound of formula (I):

wherein SWO refers to collectively the alcohols, including santalol, present in the sandalwood oil; wherein R is selected from alkyl groups of up to about 22 carbon atoms and aryl groups of up to about 22 carbon atoms and alkylene group of up to about 22 carbon atoms and an arylene group of up to about 22 carbon atoms. The alkyl, aryl and alkylene groups may be substituted or unsubstituted, branched or straight chains. In addition, R may contain heteroatoms and may be straight chained or branched.

Examples of suitable straight-chain alkyl groups in formula I include methyl, ethyl, propyl, butyl, hexyl, heptyl, octyl, dodecyl, 1-pentadecyl, 1-heptadecyl and the like groups.

Examples of suitable branched chain alkyl groups in formula I include isopropyl, sec-butyl, t-butyl, 2-methylbutyl, 2-pentyl, 3-pentyl and the like groups.

Examples of suitable cyclic alkyl groups in formula I include cyclopropyl, cyclobutyl, cyclopentyl and cyclohexyl groups.

Examples of suitable "alkenyl" groups in I and Ib include vinyl (ethenyl), 1-propenyl, i-butenyl, pentenyl, hexenyl, n-decenyl and c-pentenyl and the like.

The groups may be substituted, generally with 1 or 2 substituents, wherein the substituents are independently selected from halo, hydroxy, alkoxy, amino, mono- and dialkylamino, nitro, carboxyl, alkoxycarbonyl, and cyano groups.

By the expression "phenalkyl groups wherein the alkyl moiety contains 1 to 3 or more carbon atoms" is meant benzyl, phenethyl and phenylpropyl groups wherein the phenyl moiety may be substituted. When substituted, the phenyl moiety of the phenalkyl group may contain independently from 1 to 3 or more alkyl, hydroxy, alkoxy, halo, amino, mono- and dialkylamino, nitro, carboxyl, alkoxycarbonyl and cyano groups.

Examples of suitable "heteroaryl" in formula I are pyridinyl, thienyl or imidazolyl.

As noted herein, the expression "halo" is meant in the conventional sense to include F, Cl, Br, and I.

Among the compounds represented by the general Formula I, preferred compounds are such in which R is one of the following groups: methyl, ethyl, propyl, butyl, pentyl, hexyl, 1-pentadecyl, 1-heptadecyl, isobutyl, methoxyethyl, ethoxyethyl, benzyl and nicotinyl.

The compounds of Formula I are esters of alcohols present in sandalwood oil. Few esters of santalol such as santalyl acetate and santalyl phenyl acetate have been known in the perfume industry as fragrances. However, information in the literature do not disclose or indicate the esters of sandalwood oil or santalol have any utility as pro-drug forms suitable for oral and topical delivery for treating diseases such as cold sores and genital herpes.

The present invention also generally pertains to pharmaceutical compositions comprising one or more of the compounds set forth above.

Accordingly, one aspect of the present invention is to disclose the esters of sandalwood oil in the treatment of cold sores and genital herpes in humans.

In another aspect of this invention, the esters of the active component or components of the sandalwood oil, namely α- and β-santalols, are disclosed for the treatment of cold sores and genital herpes in humans.

Yet another aspect of the present invention is to disclose the esters of sandalwood oil, esters of α- and β-santalols in the treatment of warts caused by the human papillomavirus (HPV) in humans.

Yet in another aspect of this invention, the esters of the active component or components of the sandalwood oil, namely α- and β-santalols, are disclosed for the treatment of warts caused by the human papillomavirus (HPV) in humans.

In particular, the esters of sandalwood oil and esters of α- and β-santalols described herein may be used for the preparation of therapeutic compositions in the treatment of cold sores, genital herpes and warts induced in humans. Preferably, the compositions useful in the method may be topically applied to the human in need of such therapy.

The method of the present invention neither destroys healthy, uninfected tissue nor results in any local or systemic side effects, scarring, disfigurement or discomfort to the human treated. Furthermore, the use of the esters of the present invention reduces the occurrence of skin irritation and rashes unlike the free alcohols. The method includes the use of either ester of sandalwood oil or esters of α- and β-santalols for the administration to an area of the human which is anticipated to evidence cold sores, or an area which presently exhibits genital herpes to eliminate the sores.

In accordance with the method according to this invention, regular use of the α- and β-santalols is meant to mean application of the α- and β-santalols at least once a day to the body surface containing the cold sores or genital herpes or viral-induced tumors (i.e., warts and *Molluscom contagiosum* tumors).

There is further disclosed a method for the prevention and treatment of cold sores and genital herpes, comprising the application of a cream or douche containing either an ester of sandalwood oil or esters of α- or β-santalols or mixtures thereof, to the affected area of the human body. There is also disclosed a method for treating genital herpes, said method comprising the application of either an ester of sandalwood oil or esters of α- or β-santalols or mixtures thereof, to the genital area of a human for a period of time and at a sufficient concentration to eradicate the herpes virus from the genital area of the human.

The pharmaceutical compositions of the present invention can additionally include one or more pharmaceutically acceptable excipients. One of ordinary skill in the art would be familiar with pharmaceutically acceptable excipients. For example, the pharmaceutically acceptable excipient may be a water soluble sugar, such as mannitol, sorbitol, fructose, glucose, lactose, and sucrose.

The pharmaceutical compositions of the present invention may further comprise one or more pharmaceutically acceptable antioxidants. Any pharmaceutically acceptable antioxidant known to those of ordinary skill in the art is contemplated for inclusion in the present pharmaceutical compositions. For example, the pharmaceutically acceptable antioxidant may be selected from the group consisting of ascorbic acid, sodium ascorbate, sodium bisulfate, sodium metabisulfate and monothio glycerol.

The pharmaceutical compositions of the present invention may further comprise one or more pharmaceutically acceptable preservatives. Any pharmaceutically acceptable preservative known to those of ordinary skill in the art is contemplated for inclusion in the present pharmaceutical compositions. Examples of such preservatives include methylparaben, methylparaben sodium, propylparaben, propylparaben sodium, benzalkonium chloride, and benzthonium chloride.

The pharmaceutical compositions of the present invention may further comprise one or more pharmaceutically acceptable buffering agents. Any pharmaceutically acceptable buffering agent known to those of ordinary skill in the art is contemplated for inclusion in the present pharmaceutical compositions. Examples of such buffering agents include of monobasic sodium phosphate, dibasic sodium phosphate, sodium benzoate, potassium benzoate, sodium citrate, sodium acetate, and sodium tartrate.

The pharmaceutical compositions of the present invention can include any concentration of a compound of the present invention. For example, the concentration of compound may be 0.1 mg/ml to 4000 mg/ml or greater. In certain particular embodiments, the concentration of compound is 1 mg/ml to 500 mg/ml. In still further embodiments, the concentration of compound is 5 mg/ml to 200 mg/ml.

In some embodiments of the present invention, the pharmaceutical composition includes more than one of the novel compounds set forth above. In other embodiments of the present invention, the pharmaceutical composition includes one or more secondary therapeutic agents directed to a disease or health-related condition, as discussed below.

The present invention also generally pertains to methods of treating or preventing a pathological condition in a subject, comprising providing a therapeutically effective amount of any of the pharmaceutical compositions set forth above, and administering the composition to the subject. The subject can be any subject, such as a mammal or avian species. In certain particular embodiments, the mammal is a human. The human may be an individual affected by or at risk of developing a disease or condition amenable to therapy with sandalwood oil. For example, the pathological condition may be cold sores, genital herpes, genital warts, acne, urinary tract infection, a wound, or skin wrinkling.

The pharmaceutical composition of the present invention may be administered to the subject by any method known to those of ordinary skill in the art. For example, the method of administering the composition to the subject may include oral, topical, nasal, inhalational, rectal, or vaginal. Methods of administration are discussed in greater detail in the specification below.

In certain embodiments of the methods of the present invention, the method involves administering to the subject a therapeutically effective amount of a secondary agent. The secondary agent can be any pharmacologic agent known or suspected to be of benefit in the treatment or prevention of a disease or health-related condition in a subject. For example, in some embodiments, the secondary agent is a secondary antihyperproliferative agent. Secondary antihyperproliferative agents, which include chemotherapeutic agents, are well-known to those of ordinary skill in the art. Examples of such agents include doxorubucin, daunorubicin, mitomycin, actinomycin D, bleomycin, cisplatin, VP16, an enedyine, taxol, vincristine, vinblastine, carmustine, mellphalan, cyclophsophamide, chlorambucil, busulfan, lomustine, 5-fluorouracil, gemcitabin, BCNU, or camptothecin. The secondary agent may be an anti-viral agent. Examples of anti-viral agents include acyclovir, tetracaine, penciclovir, docosanol, and valacyclovir.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 is an illustration of the Chemical Structures of Santalols.

DESCRIPTION OF ILLUSTRATIVE EMBODIMENTS

The present invention is based on the inventors' unexpected discovery of certain derivatives of sandalwood oil and santalols that are highly lipophilic, non-irritating, and thus allow higher concentrations for improved bioavailability following administration in a cream or ointment formulations. The compounds of the present invention include esters of sandalwood oil and santalols. These compounds are suitable by any route of administration, but are particularly suited for oral or topical administration in view of their lipid solubility. These compounds thus provide for a novel form of therapy of any disease or condition wherein sandalwood oil and santalols are believed to be of benefit, cold sores, genital herpes, genital warts and urinary tract infection.

DETAILED DESCRIPTION OF THE INVENTION

A. Sandalwood oil Derivatives of the Present Invention

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification, the singular forms "a," "an" and "the" include plural referents unless the context clearly dictates otherwise. Thus, for example, reference to "a pharmacologically active agent" includes a combination of two or more pharmacologically active agents, and the like. In describing the present invention, the following terminology will be used in accordance with the definitions set out below.

The terms "active agent," "drug" and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned which also induce the desired pharmacologic effect.

The term "topical administration" is used in its conventional sense to mean delivery of a topical drug or pharmacologically active agent to the skin or mucosa.

"Carriers" or "vehicles" as used herein refer to carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner.

By an "effective" amount of a drug or pharmacologically active agent is meant a nontoxic but sufficient amount of the drug or agent to provide the desired effect.

The term "sandalwood oil" as used herein refers to the oil extracted from the woods of *santalum* species either by steam distillation or by solvent extraction method.

The term "ester of sandalwood oil" refers to the fully acylated or esterified product of sandalwood oil. The various alcohols present in the sandalwood oil is almost fully esterified and thus "ester of sandalwood oil" contains a mixture of esters.

The term "santalol" as used herein is intended to encompass not only α- and β-santalol, but any isomer or any compounded mixture thereof.

The novel compounds set forth herein are ester derivatives of sandalwood oil and santalol. These derivatives are capable of reverting to the active parent compound following enzymatic or chemical hydrolysis. These derivatives have a higher lipophilicity, lipid solubility and less irritation to the skin than the parent compound, and hence are better able to be incorporated into certain pharmaceutical formulations, including cream and ointment pharmaceutical formulations. The compounds of the present invention are set forth by the following formula:

The present invention generally pertains to a compound of formula (I):

R—CO—SWO     (I)

wherein SWO refers to collectively the alcohols, including santalol, present in the sandalwood oil; wherein R is selected from alkyl groups of up to about 22 carbon atoms and aryl groups of up to about 22 carbon atoms and alkylene group of up to about 22 carbon atoms and an arylene group of up to about 22 carbon atoms. The alkyl, aryl and alkylene groups may be substituted or unsubstituted, branched or straight chains. In addition, R may contain heteroatoms and may be straight chained or branched.

Examples of suitable straight-chain alkyl groups in formula I include methyl, ethyl, propyl, butyl, hexyl, heptyl, octyl, dodecyl, 1-pentadecyl, 1-heptadecyl and the like groups.

Examples of suitable branched chain alkyl groups in formula I include isopropyl, sec-butyl, t-butyl, 2-methylbutyl, 2-pentyl, 3-pentyl and the like groups.

Examples of suitable cyclic alkyl groups in formula I include cyclopropyl, cyclobutyl, cyclopentyl and cyclohexyl groups.

Examples of suitable "alkenyl" groups in I and Ib include vinyl (ethenyl), 1-propenyl, i-butenyl, pentenyl, hexenyl, n-decenyl and c-pentenyl and the like.

The groups may be substituted, generally with 1 or 2 substituents, wherein the substituents are independently selected from halo, hydroxy, alkoxy, amino, mono- and dialkylamino, nitro, carboxyl, alkoxycarbonyl, and cyano groups.

By the expression "phenalkyl groups wherein the alkyl moiety contains 1 to 3 or more carbon atoms" is meant benzyl, phenethyl and phenylpropyl groups wherein the phenyl moiety may be substituted. When substituted, the phenyl moiety of the phenalkyl group may contain independently from 1 to 3 or more alkyl, hydroxy, alkoxy, halo, amino, mono- and dialkylamino, nitro, carboxyl, alkoxycarbonyl and cyano groups.

Examples of suitable "heteroaryl" in formula I are pyridinyl, thienyl or imidazolyl.

As noted herein, the expression "halo" is meant in the conventional sense to include F, Cl, Br, and I.

Among the compounds represented by the general Formula I, preferred compounds are such in which R is one of the following groups: methyl, ethyl, propyl, butyl, pentyl, hexyl, 1-pentadecyl, 1-heptadecyl, isobutyl, methoxyethyl, ethoxyethyl, benzyl and nicotinyl.

The compounds of Formula I are esters of alcohols present in sandalwood oil. Few esters of santalol such as santalyl acetate and santalyl phenyl acetate have long been known in the perfume industry as fragrances. However, information in the literature do not disclose or indicate the esters of sandalwood oil or santalol have any utility as pro-drug forms suitable for oral and topical delivery for treating diseases such as cold sores and genital herpes.

B. Methods of Synthesis

The compounds of the present invention can be prepared by any method known to those of ordinary skill in the art. For example, the compounds of the present invention are esters of alcohols which are the constituents of sandalwood oil. Various methods have been described in the literature pertaining to the synthesis of a number of esters of carboxylic acids and alcohols (March's Advanced Organic Chemistry: Reactions, Mechanisms, and Structure, 5th Edition, by Michael B. Smith and Jerry March, John Wiley and Sons, Inc, 2001).

One method that has been utilized for efficient preparation of the ester of sandalwood oil of the present invention is through dissolution of the oil in methylene dichloride. Since sandalwood oil contains 80-93% of santalol, to this solution slightly in excess of 1.1 mole equivalent of anhydrous triethylamine is added with stirring at room temperature and the mixture is cooled to −5 to 0 degree. To this solution slightly in excess of 1 mole equivalent of an acid chloride is added with stirring while keeping the temperature around 5° C. After that, the solution was allowed to reach room temperature and stirred for 6-10 hours at room temperature. The organic phase was washed 3-4 times with dilute hydrochloric acid solution in a separating funnel to remove any amine present in the organic solution. The reaction mixture was then washed with equal amount of water three to four times to remove the amine and its salt in a separating funnel. The reaction mixture was then washed with equal amount of 10% sodium carbonate solution three to four times to remove the unreacted acid in a separating funnel. The reaction mixture was then washed with equal amount of water three to four times to remove the sodium carbonate in a separating funnel. The organic phase was dried with anhydrous sodium sulfate overnight and the methylene dichloride was removed in a rotary evaporator under vacuum. The resultant oil is called the ester of sandalwood oil as all of the alcohols present in the oil is converted into the corresponding ester.

Santalol has been isolated from sandalwood oil by distillation under vacuum, BP 95° C./0.5 mm Hg. The santalol was esterified by the procedure similar to the sandalwood oil described above.

C. Pharmaceutical Compositions

Certain embodiments of the present invention pertain to pharmaceutical compositions comprising the esters of sandalwood oil and santalols set forth herein.

The phrases "pharmaceutical," "pharmaceutically," or "pharmacologically acceptable" refer to molecular entities and compositions that do not produce an unacceptably adverse, allergic or other untoward reaction when administered to an animal, or human, as appropriate. As used herein, "pharmaceutical" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients to treat the disease of interest, such as other anti-cancer agents or anti-inflammatory agents, can also be incorporated into the compositions.

Pharmaceutical compositions of the present invention will include an effective amount of one or more of the ester derivatives set forth herein that is clinically determined to be useful in the treatment of the particular disease under consideration. One of ordinary skill in the art would be familiar with what type of dosage is required for treatment of the particular pathological condition that is present in the subject. No undue experimentation would be involved. When used for therapy, the compositions of the present invention are administered to subjects in therapeutically effective amounts. For example, an effective amount of the ester of sandalwood oil in a patient with cold sores may be an amount that promotes the healing of the sores. The dose will depend on the nature of the disease, the subject, the subject's history, and other factors. Preparation of such compositions is discussed in other parts of this specification.

As discussed above, the derivatives set forth herein have greater lipophilicity and less irritation to the skin than sandalwood oil and santalols. One advantage of these esters is that they can be incorporated into a cream or ointment form at a higher percentage by weight as compared to sandalwood oil and santalols. Another advantage is that these compositions have a very low toxicity and irritation to the skin as compared to formulations of sandalwood oil and santalol.

The compositions of the sandalwood oil and santalol derivatives of the present invention can be delivered by any method known to those of ordinary skill in the art. For example, the pharmaceutical compositions can be delivered by topical or oral delivery routes.

Compositions employing the esters of sandalwood oil and santalol set forth herein will contain a biologically effective amount of the derivative. As used herein a biologically effective amount of a compound or composition refers to an amount effective to alter, modulate or reduce disease conditions. One of ordinary skill in the art would be familiar with methods of determining a biologically effective amount of a therapeutic agent. For example, a biologically effective amount may be about 0.1 mg/kg to about 50 mg/kg or greater The therapeutic esters of sandalwood oil and santalol of the present invention may be administered alone or in combination with one or more additional therapeutic esters of the present invention. In other embodiments, the therapeutic ester of sandalwood oil and santalol is administered in combination with one or more secondary forms of therapy directed to the disease or condition to be treated. These are discussed in greater detail below. Additional pharmaceutical compounds may be administered in the same pharmaceutical composition, or in a separate dosage form, such as in a separate oral, intramuscular, or intravenous dosage forms taken at the same time.

The therapeutic agents of the present invention may be supplied in any form known to those of ordinary skill in the art. For example, the therapeutic agent may be supplied as a liquid or as a solution. The pharmaceutical compositions may contain a preservative to prevent the growth of microorganisms. It must be chemically and physically stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like.

The formulations according to the invention having been described herein may influence the ordinarily skilled artesian to make similar formulations using components that will be known in the art, without departing from the invention which is claimed herein.

The pharmaceutical formulations of the esters of sandalwood oil and santalol according to the present invention offer several advantages over the existing formulations. They can be topically applied and relatively high concentrations of the esters of sandalwood oil and santalol can be loaded into patients with high bioavailability. Thus the frequency of dosage can be reduced. Thus within the spirit, the invention is related to improved formulations and methods of using the same when administering such formulations to patients. As mentioned herein above a number of excipients may be appropriate for use in the formulation which comprise the composition according to the present invention. The inclusion of excipients and the optimization of their concentration for their characteristics such as for example ease of handling or carrier agents will be understood by those ordinarily skilled in the art not to depart from the spirit of the invention as described herein and claimed herein below.

Following preparation of the pharmaceutical compositions of the present invention, it may be desirable to quantify the amount of the esters of sandalwood oil and santalol in the pharmaceutical composition. Methods of measuring concentration of a drug in a composition include numerous techniques that are well-known to those of skill in the art. Selected examples include chromatographic techniques. There are many kinds of chromatography which may be used in the present invention: drug-specific assays, adsorption, partition, ion-exchange and molecular sieve, and many specialized techniques for using them including column, paper, thin-layer chromatography, gas chromatography, and high performance liquid chromatography (HPLC). One of ordinary skill in the art would be familiar with these and other related techniques.

D. Moisturizing Agents

Certain topical formulations of the present invention may contain moisturizing agents. Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturization factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, *aloe barbadensis*, *aloe-barbadensis* extract, *aloe barbadensis* gel, *althea officinalis* extract, aluminum starch octenylsuccinate, aluminum stearate, apricot (*prunus armeniaca*) kernel oil, arginine, arginine aspartate, *arnica montana* extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, calendula officinalis extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*)oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *eucalyptus globulus* oil, evening primrose (*oenothera biennis*) oil, fatty acids, fructose, gelatin, *geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, magnesium stearate, magnesium sulfate, maltitol, matricaria (*chamomilla recutita*) oil, methyl glucose sesquistearate, methylsilanol PCA, microcrystalline wax, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-I 5 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, serine, serum protein, sesame (*sesamum indicum*) oil, shea butter (*butyrospermum parkii*), silk powder, sodium chondroitin sulfate, sodium DNA, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

E. Antioxidants

Certain topical formulations of the present invention may also contain one or more antioxidants. Non-limiting examples of antioxidants that can be used with the compositions of the present invention include acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

F. Pathological Conditions to be Treated or Prevented

As noted in other parts of this specification, there is substantial evidence that sandalwood oil and santalol would be beneficial in the treatment of a wide variety of pathological conditions. The term "treat" or "treatment" means that the symptoms associated with one or more conditions mentioned above are alleviated or reduced in severity or frequency and the term "prevent" means that subsequent occurrences of such symptoms are avoided or that the frequency between such occurrences is prolonged.

Conditions amenable to treatment or prevention with sandalwood oil are specifically detailed in Berencia et al. (1999), Dwivedi et al. (1997), Blumenthol (1998), Okugawa et al. (1995), Bourke (1973), Nadkarni (1976), Kirtikar et al. (1993), U.S. Pat. No. 6,132,756, U.S. Pat. No. 6,406,706 and Aggarwal et al. (2003C), which have been specifically incorporated by reference in the section pertaining to curcumin, and are specifically incorporated by reference for purposes of this section.

Examples of pathological conditions responsive to sandalwood oil and santalol therapy include, but are not limited to, gonorrhea, bronchitis, sore throat, persistent cough, fever, pain and warts caused by the human papillomavirus (HPV) in humans. In test tube studies, sandalwood oil was found to slow the growth of herpes virus (Benencia 1999). An intriguing animal study found that components isolated from sandalwood caused responses similar to those seen with medications used to treat schizophrenia (Okugawa 1995). The sandalwood oil displayed chemoprotective effects on 7,12-dimethylbenz(a)anthracene-(DMBA)-initiated and 12-O-tetradecanoyl phorbol-13-acetate(TPA)-promoted skin papillomas, and TPA-induced ornithine decarboxylase (ODC) activity in mice. Treatment with sandalwood oil significantly decreased papilloma incidence by 67%, multiplicity by 96%, and TPA-induced ODC activity by 70% (Dwivedi and Abu-Ghazaleh. 1997). The sandalwood oil was found to enhance glutathione S-transferase (GST) activity and acid soluble sulphydryl (SH) levels in the liver of adult male Swiss albino mice, suggesting a possible chemopreventive action (Banerjee et al. 1993). Sandalwood oil is said to act as an antiseptic in the urinary system (Blumenthal 1998) and it might help to rid the body of the bacteria that cause these infections (Leung 1996)

It is expected that the novel ester derivatives of sandalwood oil and santalol set forth herein would be beneficial in the treatment and prevention of any of the diseases set forth above. One of ordinary skill in the art would be familiar with the many diseases and conditions that would be amenable to treatment with one or more of the ester derivatives of sandalwood oil and santalol set forth herein.

G. Secondary Therapies

Some embodiments of the claimed methods of the present invention involve administering to the subject a secondary form of therapy in addition to one or more of the therapeutic ester derivatives of sandalwood oil and santalol set forth herein. For example, if the disease is a hyperproliferative disease, such as cancer, the secondary therapy may be a chemotherapeutic agent, radiation therapy, surgical therapy, immunotherapy, gene therapy, or other form of anticancer therapy well-known to those of ordinary skill in the art. If the disease is an inflammatory disease such as arthritis, exemplary secondary forms of therapy include non-steroidal anti-inflammatory agents, steroids, and immunosuppressant therapy.

In order to increase the effectiveness of the therapeutic agent disclosed herein, it may be desirable to combine the therapeutic agent of the present invention with the secondary therapeutic agent. These compositions would be provided in a combined amount effective to provide for a therapeutic response in a subject. One of ordinary skill in the art would be able to determine whether the subject demonstrated a therapeutic response. This process may involve administering the therapeutic agent of the present invention and the secondary therapeutic agent to the subject at the same time. This may be achieved by administering a single composition or pharmacological formulation that includes both agents, or by administering two distinct compositions or formulations, at the same time, wherein one composition includes the curcumin derivative of the present invention and the other includes the secondary agent.

Alternatively, the therapeutic agent of the present invention may precede or follow the treatment with the secondary agent by intervals ranging from minutes to weeks. In embodiments where the secondary agent and the curcumin derivative of the present invention are separately administered, one would generally ensure that a significant period of time did not expire between the time of each delivery, such that the secondary agent and the therapeutic agent of the present invention would still be able to exert a beneficial effect on the subject. In such instances, it is contemplated that one may administer both modalities within about 24-48 h of each other and, more preferably, within about 12-24 h of each other, and even more preferably within about 30 minute-6 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, the therapeutic agent of the present invention is "A" and the secondary agent, such as chemotherapy, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the compositions of the present invention to a patient will follow general protocols for the administration of therapeutic agents, such as chemotherapy where the disease to be treated is cancer. It is expected that the treatment cycles would be repeated as necessary.

H. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Preparation of Propionyl Ester of Sandalwood Oil (Formula I, R=$C_2H_5$)

A mixture of 100 ml (~0.4M of alcohol content) of sandalwood oil (Spectrum Chemicals), 83.5 ml (0.6M) of anhydrous triethylamine (Spectrum Chemicals) and 200 ml of anhydrous dichloromethane was placed into a 1000 ml 2-neck round bottomed flask. The content was covered with aluminum foil to protect it from light exposure. The flask was fitted with a condenser fitted with a moisture trap on the top and a dropwise addition funnel. The flask was cooled to 0 degree centigrade in a dry ice bath and 43.5 ml (0.5M) of propionyl chloride was added from the funnel into the mixture slowly with stirring. After the addition, the mixture was allowed to reach the room temperature and stirred for 3-5 hours. The mixture was transferred into a separating funnel and washed successively with 2×500 ml of water, 2×500 ml of dilute hydrochloric acid, 2×500 ml 10% sodium carbonate solution and 3×500 ml of type I water. The organic layer was separated, dried with anhydrous magnesium sulfate and the dichloromethane was removed under vacuum to produce a clear, slightly yellow oil (95% of theoretical).

Example 2

Preparation of Propionyl Ester of Santalol (Formula I, R=$C_2H_5$)

Santalol was prepared by fractional distillation of sandalwood oil (Spectrum Chemicals) under vacuum as described in the literature. A mixture of 100 ml (~0.375M) of santalol, 83.5 ml (0.6M) of anhydrous triethylamine (Spectrum Chemicals) and 200 ml of anhydrous dichloromethane was placed into a 1000 ml 2-neck round bottomed flask. The content was covered with aluminum foil to protect it from light exposure. The flask was fitted with a condenser fitted with a moisture trap on the top and a dropwise addition funnel. The flask was cooled to 0 degree centigrade in a dry ice bath and 43.5 ml (0.5M) of propionyl chloride was added from the funnel into the mixture slowly with stirring. After the addition, the mixture was allowed to reach the room temperature and stirred for 3-5 hours. The mixture was transferred into a separating funnel and washed successively with 3×500 ml of water, 2×500 ml of dilute hydrochloric acid, 2×500 ml of 10% sodium carbonate solution and 3×500 ml of type I water. The organic layer was separated, dried with anhydrous magnesium sulfate and the dichloromethane was removed under vacuum to produce clear and slightly yellow oil (~95% of theoretical).

Example 3

Preparation of Hexanoyl Ester of Sandalwood Oil (Formula I, R=$CH_3$—$(CH_2)_4$)

The compound was prepared essentially as described in Example 1, using n-hexanoyl instead of propanoyl. The product was recovered as a yellow oil.

Example 4

Preparation of Butyryl Ester of Santalol (Formula Ib, R=$CH_3$—$(CH_2)_2$)

The compound was prepared essentially as described in Example 1, using butyryl instead of propanoyl chloride. The product was recovered as a yellow oil.

Example 5

Preparation of Butyryl Ester of Sandalwood oil (Formula I, R=$CH_3$—$(CH_2)_2$)

The compound was prepared essentially as described in Example 1, using butyryl instead of propanoyl. The product was recovered as a yellow oil.

Example 6

Preparation of Hexanoyl Ester of Santalol (Formula Ib, R=$CH_3$—$(CH_2)_4$)

The compound was prepared essentially as described in Example 1, using n-hexanoyl instead of propanoyl chloride. The product was recovered as a yellow oil.

Example 7

Preparation of Palmitoyl Santalol (Formula Ib, $R_1$=$R_2$=$CH_3$ $(CH_2)_{14}$)

The compound was prepared essentially as described in Example 1, using palmitoyl chloride instead of propanoyl chloride. The product was recovered as a slightly yellow waxy solid.

Example 8

Preparation of Gel Containing Propanoyl Ester of Sandalwood Oil

The following procedure was used to prepare a 15% gel containing propanoyl ester of sandalwood oil.

Preparation of Base Gel, Part A
In a clean container, add and mix

| | |
|---|---|
| Purified water | 600 ml |
| Potassium sorbate | 1.0 g |
| Methyl paraben sodium | 2.0 g |
| Propyl paraben sodium | 0.2 g |
| Disodium edetate | 5.0 g |
| Xantahan gum | 3.0 g |
| Carbopol Ultrez10 | 30.0 g |

Preparation of Organic Phase, Part B
In another glass container, add and dissolve at 45-50 degrees C.,

| | |
|---|---|
| Tween 80 | 0.6 g |
| Hallbrite BHB | 20.0 g |
| Propanoyl ester of sandalwood oil | 150.0 g |
| Isobornyl acetate | 5.0 g |
| Ascorbyl Palmitate | 3.0 g |
| Cetyl palmitate | 20.0 g |

Add part B to Part A and mix well in a blender
Add and mix,

| | |
|---|---|
| Triethanolamine | 16.0 g |
| Purified water to q.s | 1000 g |

Further homogenize the gel in a high pressure homogenizer.

The pH of the gel is 6.0-6.5. The gel is smooth and white in color.

Example 9

Preparation of Oil-in-Water Emulsion Containing Santalyl Propionate

Propanoyl Santalol

The following procedure was used to prepare a 15% gel containing propanoyl ester of santalol.

Preparation of Base Gel, Part A
In a clean container, add and mix

| | |
|---|---|
| Purified water | 600 ml |
| Potassium sorbate | 1.0 g |
| Methyl paraben sodium | 2.0 g |
| Propyl paraben sodium | 0.2 g |
| Disodium edetate | 5.0 g |
| Xantahan gum | 3.0 g |
| Carbopol Ultrez10 | 30.0 g |

Preparation of Organic Phase, Part B
In another glass container, add and dissolve at 45-50 degrees C.,

| | |
|---|---|
| Tween 80 | 0.6 g |
| Hallbrite BHB | 20.0 g |
| Propanoyl ester of santalol | 150.0 g |
| Isobornyl acetate | 5.0 g |
| Ascorbyl Palmitate | 3.0 g |
| Cetyl palmitate | 20.0 g |

Add part B to Part A and mix well in a blender
Add and mix,

| | |
|---|---|
| Triethanolamine | 16.0 g |
| Purified water to q.s | 1000 g |

Further homogenize the gel in a high pressure homogenizer.

The pH of the gel is 6.0-6.5. The gel is smooth and white in color.

Example 10

Preparation of Topical Cream Containing 20% Santalyl Acetate

Ethanoyl Santalol

A skin cream composition containing santalyl acetate is shown in Table 4, and lists the ingredients in the compositions containing diethyl-azelate. The top portion of Table III shows the proportions of the base, and the bottom portion shows the constituents and proportions of the additives and all proportions are in units of percent by weight. As shown in Table III, the base consists of a commercially available moisturizing skin lotion and the additive consists of santalyl acetate. The base and the additives were mixed thoroughly in a blender to prepare the cream.

TABLE III

Topical Cream Composition for Santalyl Acetate

| COMPOSITION INGREDIENT NAME | % |
|---|---|
| A. BASE INGREDIENT | |
| Lubriderm Moisturizing Lotion sold by Pfizer Healthcare Product Newhaven, Connecticut | 80.0 |
| B. ADDITIVES | |
| Santalyl Acetate | 20.0 |
| TOTAL ADDITIVES | 20.0 |

Example 11

Preparation of Oil Containing 20% Santalyl Propionate

Propanoyl Santalol

An oil composition containing santalyl propionate is shown in Table 6, and lists the ingredients in the compositions containing santalyl propionate. The top portion of Table IV shows the proportions of the base, and the bottom portion shows the constituents and proportions of the additives and all proportions are in units of percent by weight. As shown in Table IV, the base consists of a commercially available ethyl octanoate and the additive consists of santalyl propionate. The base and the additives were mixed thoroughly to prepare the oil suitable for skin application.

TABLE IV

Topical oil Composition for Santalyl Propionate

| COMPOSITION INGREDIENT NAME | Percent |
|---|---|
| A. BASE INGREDIENT | |
| Ethyl Octanoate sold by Sigma Aldrich St. Louis, Missouri | 80.0 |
| B. ADDITIVES | |
| Santalyl propionate | 20.0 |
| TOTAL ADDITIVES | 20.0 |

Example 12

Toxicity Assessment of the Inventive Composition

A 20% solution of santalyl propionate as described in example 11, was applied to the forearm of 10 healthy individuals twice daily for a two-week period in an outpatient clinic. No patients complained of burning, irritation, scaling or redness after the cream. Patients returned to the clinic after having used the solution for two weeks for a visual inspection of the forearm area. The examining physician noted no redness, irritation or scaling in the area where the solution had been applied.

Example 13

Case I

Patient with Cold Sores Treated with 20% Oil of Santalyl Propionate

A 21 year old male has developed cold sores on his mouth with reddish blisters and pain. He was given the 20% oil of santalyl propionate and the following is his testimony on the effectiveness of the oil for the treatment of cold sores. "On 8 Feb. 2006, I was given a sample solution to treat cold sores I had acquired on my lower lip. I was informed to apply it a couple times a day and it would begin to clear. I began about 7 p.m. by rubbing a few drops on the surface of the sore. I applied it once more before I slept and again in the morning. By morning time I had noticed a reduction in the color of the sore. It had gone from an unsightly, irritated flesh color to a more neutral tone. I repeated applications twice more that day and by that evening I had noticed a few other details. The product moistened my lip so the scab of the cold sore was not apparent. Tenderness and swelling had diminished as well as the overall diameter of the original sore. Within 24 hours it had appeared that the cold sore was almost gone. My cold sores generally take close to two weeks to heal if left untreated and with this medication it appeared to have disappeared in about 2 days of treatment. By the $48^{th}$ hour of treatment my sore had been almost completely wiped out and my normal skin tone had returned".

Case II

Patient with Cold Sores Treated with 20% Oil of Santalyl Propionate

A 45 year old male developed cold sores on his mouth and was treated with the 20% oil of santalyl propionate. He gave the following testimony about the treatment. "I recently tried a topical solution for the treatment of cold sores/fever blisters on my lip. I applied a small amount of the solution (approximately 2-3 drops) to the cold sores/fever blisters then rubbed the solution into them and immediately experienced a drying effect of theses cold sores/fever blisters. I repeated this application a few times a day and within three to four days the cold sores/fever blisters were healed. I experience theses cold sores/fever blisters every couple of years or so, I do not suffer from them on a regular basis. They occur when I become run down from a combination of overworking, lack of sleep, poor diet and lack of exercise; basically when I run my immune system down. I have tried over the counter medication and prescription medications in the past and nothing has worked so effectively as the solution I received. I would recommend this solution to anyone who suffers from occasional or reoccurring cold sores/fever blisters. These sores are embarrassing and debilitating to a person's self-confidence and their ego. The solution is extremely effective and works quickly to dry and clear the sores. If any additional information is required, I will make myself available to inquiry.

Case III

Patient with Cold Sores Treated with 15% Cream of Sandalwood Oil Propionate A 40 year old female developed cold sores on her mouth and was treated with the 15% cream of sandalwood oil propionate. She gave the following testimony about the treatment. "I use to get cold sores every 3-4 months and it would give me pain and redness around my mouth. I recently tried a topical cream for the treatment of cold sores/fever blisters on my lip. I started applying a small amount of the cream to the cold sores/fever blisters then rubbed the cream into them and sensed a drying effect within an hour of theses cold sores/fever blisters. I used this application a few times a day and within three to four days the cold sores/fever blisters were healed. This cream is much better than the medication I have tried before obtained over the counter and nothing has worked so effectively as the cream I used".

Case IV

Patient with Herpes Treated with 15% Cream of Sandalwood Oil Propionate

A 65 year old female developed herpes outbreak around her vaginal area and was treated with the 15% cream of sandalwood oil propionate. She gave the following testimony about the treatment. "I used to get herpes outbreak around my vaginal area with blisters few times every year and I used the cream provided to me to treat my herpes blisters. I applied the thoroughly on the affected area 2-3 times a day and I noticed that the blisters strated drying within 3 days. After a week of application, it is completely gone and I would be very happy to recommend this wonderful cream for any person who suffers from herpes blisters".

Case V

Patient with Cold Sores Herpes Treated with 15% Cream of Sandalwood Oil Propionate A female clinical surgical nurse had cold sore blisters and she was provided with the 15% cream of sandalwood oil propionate. She had provided the following testimony. "I have struggled with cold sores on my lower lip since I was 18 years old. I have tried every over the counter product out there and prescription medicines. In the past, it usually takes anywhere from one to two weeks for the cold sore to heal stop hurting. Many of the medicines, I have tried have caused quite a bit of discomfort upon application. I had convinced myself that there was not anything out there that could painlessly heal my cold sore in less than a week. I was overjoyed when I tried the cold sore cream given to me as a sample. This cream did not cause pain upon application and kept my lip soft through out the healing process. Amazingly, my cold sore was completely gone in about 30-36 hours. I have never had cold core heal that quickly. This cold sore cream also has a very pleasant taste. Thank you for allowing me to try this cream".

REFERENCES

1. Blumenthal M, ed. *The complete German Commission E monographs, Therapeutic Guide to Herbal Medicines.* Austin, Tex.: American Botanical Council; Boston, Mass.: Integrative Medicine Communications; 1998: 118.
2. Leung A, Foster S. *Encyclopedia of Common Natural Ingredients Used in Food, Drugs, and Cosmetics.* New York, N.Y.: John Wiley & Sons; 1996: 460-461.
3. Benencia F, Courreges M C. Antiviral activity of sandalwood oil against Herpes simplex viruses-1 and -2. *Phytomedicine.* 1999; 6:135-139.
4. Okugawa H, Ueda R, Matsumoto K, et al. Effect of alpha-Santalol and beta-Santalol from sandalwood on the central nervous system in mice. *Phytomedicine.* 1995; 2:119-126.

5. Sandra A, Shenoi S D, Srinivas C R. Allergic contact dermatitis from red sandalwood (*Pterocarpus santalinus*). *Contact Dermatitis.* 1996; 34:69.
6. Sharma R, Bajaj A K, Singh K G. Sandalwood dermatitis. *Int J Dermatol.* 1987; 26:597.
7. Hayakawa R, Matsunaga K, Arima Y. Depigmented contact dermatitis due to incense. *Contact Dermatitis.* 1987; 16:272-274.
8. Banerjee, S et al. 1993. Modulatory influence of sandalwood oil on mouse hepatic glutathione S-transferase activity and acid soluble sulphydryl level. *Cancer Lett.* February; 68(2-3):105-9.
9. Bourke, E. L. et al. 1973. A hypotensive agent in *Santalum ellipticum. Planta Med.* March; 23(2):110-4.
10. Dash, Bhagwan. 1991. *Materia Medica of Ayurveda.* New Delhi: B. Jain Publishers. Frawley, David and Vasant Lad. 1986. *The Yoga Of Herbs: An Ayurvedic Guide to Herbal Medicine.* Santa Fe: Lotus Press.
11. Dwivedi, C and A. Abu-Ghazaleh. 1997. Chemopreventive effects of sandalwood oil on skin papillomas in mice. *Eur J Cancer Prev.* August; 6(4):399-401.
12. Jones G. P. et al. 1994. Effect of feeding quandong (*Santalum acuminatum*) oil to rats on tissue lipids, hepatic cytochrome P-450 and tissue histology. *Food Chem Toxicol.* June; 32(6):521-5.
13. Kirtikar K R and B D Basu. 1993. *Indian Medicinal Plants.* 2nd ed. Vol. 1-4. 1935. Reprint. Delhi: Periodical Experts.
14. Nadkarni, Dr. K. M. 1976. *The Indian Materia Medica, with Ayurvedic, Unani and Home Remedies.* Revised and enlarged by A. K. Nadkarni. 1954. Reprint. Bombay: Bombay Popular Prakashan PVP.
15. Varrier, P. S. 1996. *Indian Medicinal Plants: A Compendium of 500 species.* Edited by P K Warrier, Vata/Pitta/Kapha Nambiar and C Ramankutty. vol 5. Hyderabad: Orient Longman.]
16. Boon R, et al. (2000). Penciclovir cream for the treatment of sunlight-induced herpes simplex labialis: A randomized, double-blind, placebo-controlled trial. *Clinical Therapeutics,* 22(1): 76-90.
17. Habif T P (2004). Herpes simplex. In *Clinical Dermatology: A Color Guide to Diagnoses and Therapy,* 4th ed., pp. 381-387. Philadelphia: Mosby.
18. Sacks S L, et al. (2001). Clinical efficacy of topical doscosanol 10% cream for herpes simplex labialis: A multicenter, randomized, placebo-controlled trial. *Journal of the American Academy of Dermatology,* 45: 222-230.
19. Herpes labialis (2003). *Clinical Evidence* (9): 1836-1841.
20. Habif T P, et al. (2001). Herpes simplex (cold sores, fever blisters). In *Skin Disease Diagnosis and Treatment,* pp. 160-163. St. Louis Mosby.
21. Dwivedi C et al. (2003). Chemopreventive Effects of -Santalol on Skin Tumor Development in CD-1 and SENCAR Mice Cancer. Epidemiology Biomarkers & Prevention, 12: 151-156.
22. Kaur M et al. (2005). Skin cancer chemopreventive agent, -santalol, induces apoptotic death of human epidermoid carcinoma A432 cells via caspase activation together with dissipation of mitochondrial membrane potential and cytochrome c release. Carcinogenesis, 26(2):369-380.

We claim:

1. A method for treating cold sores and genital herpes induced by the infection of herpes simplex viruses (HSV-1 and HSV-2) in a mammal, said method comprising application to said mammal of a therapeutically effective amount of a pharmaceutical composition containing an ester of sandalwood oil of formula (I):

wherein SWO refers to collectively the alcohols, including santalol, present in the sandalwood oil; wherein R is selected from alkyl groups of up to about 22 carbon atoms and aryl groups of up to about 22 carbon atoms and alkylene group of up to about 22 carbon atoms and an arylene group of up to about 22 carbon atoms, wherein all of said alcohols in said oil are fully esterified.

2. The ester of sandalwood oil of claim 1 wherein R is a methyl group.

3. The method of claim 1, wherein the pharmaceutical composition is comprised in a topical formulation.

4. The method of claim 3, wherein the topical formulation is a cream.

5. The method of claim 1, wherein the pharmaceutical composition comprises one or more additional pharmaceutical agents.

6. The method of claim 5, wherein the one or more additional pharmaceutical agents is one or more fungicidal or fungistatic agents.

7. The method of claim 5, wherein the one or more additional pharmaceutical agents is one or more bacteriocidal or bacteriostatic agents.

8. The method of claim 5, wherein the one or more additional pharmaceutical agents is one or more viricidal or viristatic agents.

9. The method of claim 5, wherein the one or more additional pharmaceutical agents is one or more cytotoxic agents.

10. The method of claim 1, wherein the composition is a pharmaceutical composition further comprising one or more pharmaceutically acceptable excipients.

11. The method of claim 10, wherein the excipients include one or more pharmaceutically acceptable antioxidants.

12. The method of claim 11, wherein the antioxidant is selected from the group consisting of ascorbic acid, sodium ascorbate, sodium bisulfite, sodium metabisulfate, curcumin, curcumin derivatives, ursolic acid, resveratrol, resveratrol derivatives, alpha-lipoic acid and monothioglycerol.

13. The method of claim 10, wherein the excipients are selected from the group consisting of pharmaceutically acceptable preservatives and buffering agents.

14. The method of claim 13, wherein the buffering agent is selected from the group consisting of monobasic sodium phosphate, dibasic sodium phosphate, sodium benzoate, potassium benzoate, sodium citrate, sodium acetate and sodium tartrate.

15. The method of claim 13, wherein the preservative is selected from the group consisting of methylparaben, methylparaben sodium, propylparaben, propylparaben sodium, benzalkonium chloride and benzthonium chloride.

16. The method of claim 1, wherein the composition comprises one or more pharmaceutically acceptable polysaccharides.

17. The method of claim 16, wherein the polysaccharide is selected from the group consisting of dextran sulfate, pectin, modified pectin, insoluble 1,3-β-D glucan, micronized 1,3-β-D glucan, soluble 1,3-β-D glucan, phosphorylated 1,3-β-D glucan, aminated 1,3-β-D glucan and carboxymethylated 1,3-β-D glucan, sulfated 1,3-β-D glucan, insoluble 1,3/1,6-β-D glucan, micronized 1,3/1,6-β-D glucan, soluble 1,3/1,6-β-D glucan, phosphorylated 1,3/1,6-β-D glucan, aminated 1,3/1,6-β-D glucan and carboxymethylated 1,3/1,6-β-D glucan or sulfated 1,3/1,6-β-D glucan.

18. The method of claim 1 wherein the mammal is a human.

19. The method of claim 1, wherein the composition is administered orally, nasally, topically, rectally or vaginally.

20. The method of claim 1 where the alkyl, aryl and alkylene groups may be substituted.

21. The method of claim 1 where the alkyl, aryl and alkylene groups may be unsubstituted.

22. The method of claim 1 where the alkyl, aryl and alkylene groups may be branched chains.

23. The method of claim 1 where the alkyl, aryl and alkylene groups may be straight chains.

24. The method of claim 1 where the R may contain heteroatoms such as O, N, Cl, F, Br, I and S.

25. The method of claim 1 where the R may be a straight chain.

26. The method of claim 1 where the R may be a branched chain.

* * * * *